United States Patent [19]

Hayashi et al.

[11] 4,052,512

[45] * Oct. 4, 1977

[54] PROSTAGLANDIN ANALOGUES

[75] Inventors: Masaki Hayashi; Seiji Kori; Hirohisa Wakatsuka, all of Takatsuki, Japan

[73] Assignee: Ono Pharmaceutical Company, Osaka, Japan

[*] Notice: The portion of the term of this patent subsequent to Jan. 6, 1993, has been disclaimed.

[21] Appl. No.: 646,316

[22] Filed: Jan. 5, 1976

[51] Int. Cl.$^2$ ............... C07C 177/00; A61K 31/19; A61K 31/215

[52] U.S. Cl. .............. 424/305; 260/514 D; 424/317; 560/121

[58] Field of Search ............. 260/468 D, 514 D, 14; 424/305, 317

[56] References Cited

U.S. PATENT DOCUMENTS 3,931,296   1/1976   Hayashi et al. .............. 260/514

FOREIGN PATENT DOCUMENTS 2,365,035   7/1974   Germany ................. 260/468

*Primary Examiner*—Robert Gerstl
*Attorney, Agent, or Firm*—Albert H. Graddis; Frank S. Chow

[57] ABSTRACT

New trans-$\Delta^2$-prostaglandins of the formula

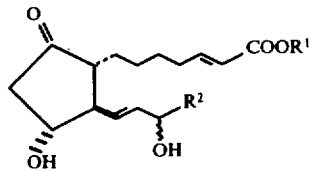

(wherein $R^1$ represents a hydrogen atom or a straight- or branched-chain alkyl group containing from 1 to 10 carbon atoms, $R^2$ represents a 1,1-dimethyl-pentyl group or a 2-ethylheptyl group, the wavy line ∿ indicates attachment of the depicted group in α-configuration or racemic form consisting of equimolecular mixtures of α-configuration and β-configuration and the $C_2$-$C_3$ and $C_{13}$-$C_{14}$ double bonds are trans), which are useful for the treatment of hypertension, contraception menstrual regulation.

3 Claims, No Drawings

PROSTAGLANDIN ANALOGUES

This invention relates to a new process for the preparation of prostaglandin analogues, and to new prostaglandin analogues and compositions containing them.

Prostaglandins are derivatives of prostanoic acid which has the following formula:

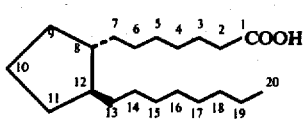

Various types of prostaglandins are known, the types depending inter alia on the structure and substituents on the alicyclic ring. For example, the alicyclic rings of prostaglandins E(PGE), F(PGF) and A(PGA) have the structures:

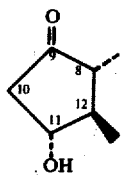

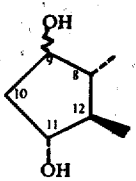

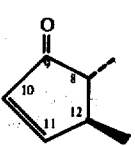

respectively.

Such compounds are sub-classified according to the position of double bond(s) in the side chain(s) attached to the 8- and 12-positions of the alicyclic ring. Thus PG-1 compounds have a trans-double bond between $C_{13}$–$C_{14}$ (trans-$\Delta^{13}$) PG-2 compounds have a cis-double bond between $C_5$–$C_6$ and a trans-double bond between $C_{13}$–$C_{14}$ (cis-$\Delta^5$, trans-$\Delta^{13}$), and PG-3 compounds have cis-double bonds between $C_5$–$C_6$ and $C_{17}$–$C_{18}$ and a trans-double bond between $C_{13}$–$C_{14}$ (cis-$\Delta^5$, trans-$\Delta^{13}$, cis-$\Delta^{17}$). For example, prostaglandin $F_1\alpha$ (PGF$_1\alpha$) and prostaglandin $E_1$ (PGE$_1$) are characterized by the following structures V and VI.

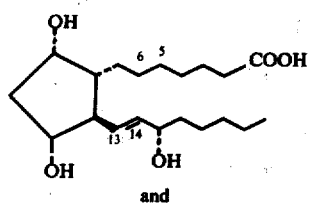

and

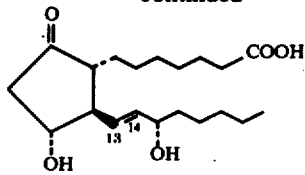

respectively. The structures of PGF$_2\alpha$ and PGE$_2$, as members of the PG-2 group, correspond to those of formulae V and VI respectively with a cis-double bond between the carbon atoms in positions 5 and 6. Compounds in which the double bond between the carbon atoms in positions 13 and 14 of members of the PG-1 group is replaced by ethylene (—CH$_2$CH$_2$—) are known as dihydro-prostaglandins, e.g. prostaglandin-$F_1\alpha$ (dihydro-PGF$_1\alpha$) and prostaglandin $E_1$ (dihydro-PGE$_1$).

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyper-lipemia. PGE$_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammals. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade processes have been developed for the preparation of compounds analogous to natural prostaglandins or derivatives of prostaglandins in order to discover inter alia new products possessing the pharmacological properties of the 'natural' prostaglandins or one or more of such properties to an enhanced degree. It has been found that small changes of chemical structure from the natural prostaglandins can considerably alter the pharmacological properties of the prostaglandins and can, in numerous instances, destroy therapeutic utility.

A process is known for the preparation of a prostaglandin analogous to PGE$_1$ in which there is a trans double bond between $C_2$-$C_3$, i.e. trans-$\Delta^2$-$PGE_1$, of the formula

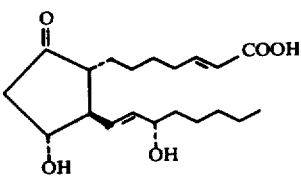

VII

The process, which is described in Van Dorp in Annals New York Academy of Sciences, 180, 185 (1971), is based on a biosynthetic reaction involving incubating sheep seminal vesicular glands with an unsaturated fatty acid as substrate, according to the reaction scheme:

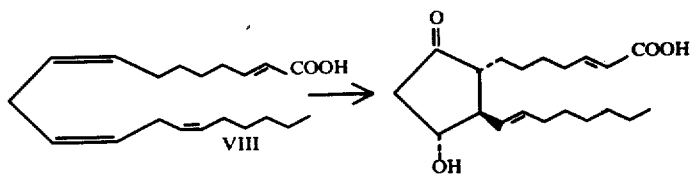

However, this process is difficult and expensive to carry out on a large scale due to the complicated synthesis of the unsaturated fatty acid and the use of expensive materials of animal origin of difficult availability.

As a result of research and experimentation a new process has been evolved for the preparation of trans-$\Delta^2$-$PGE_1$, and of other prostaglandins having a trans $C_2$-$C_3$ double bond which possess the pharmacological properties of the natural prostaglandins to the same extent or to an enhanced degree, which process avoids the use of expensive materials derived from sheep and employs readily obtainable starting materials.

The present invention is concerned with trans-$\Delta^2$-prostaglandin analogues of the general formula:

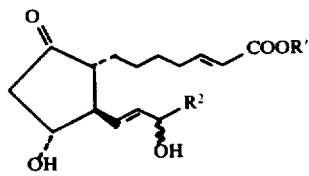

IX (wherein $R^1$ represents a hydrogen atom or a straight- or branched-chain alkyl group containing from 1 to 10 carbon atoms, $R^2$ represents a 1,1-dimethylpentyl group or a 2-ethylheptyl group, the wavy line ∿∿ indicates attachment of the depicted group in α-configuration or racemic form consisting of equimolecular mixtures of α-configuration and β-configuration and the $C_2$-$C_3$ and $C_{13}$-$C_{14}$ double bonds are trans) and cyclodextrin clathrates of such acids and esters, and when $R^1$ represents a hydrogen atom, non-toxic (e.g. sodium) salts thereof.

The present invention is concerned with all compounds of general formula IX in the natural form.

As will be apparent to those skilled in the art, the compounds depicted in general formula IX have three centers of chirality, these three centers of chirality being at the alicyclic ring carbon atoms identified as 8 and 12 and at the C-15 carbon atoms which has attached to it a hydroxy group. A further center of chirality occurs when the symbol $R^2$ represents a 2-ethylheptyl group. The presence of chirality leads, as is well known, to the existence of isomerism. However the compounds of general formula IX all have such a configuration that the side chains attached to the ring carbon atoms in the positions identified as 8 and 12 are trans with respect to each other. Accordingly, all isomers of general formula IX, and mixtures thereof, which have those side-chains attached to the ring carbon atoms in positions 8 and 12 in the trans configuration and have a hydroxy group in the 15-position are to be considered within the scope of general formula IX.

According to the present invention, the trans-$\Delta^2$-prostaglandins of general formula IX are prepared by the process which comprises reacting a cyclopentane derivative of the general formula:

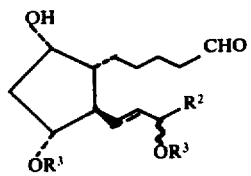

X (wherein $R^3$ represents a 2-tetrahydropyranyl group unsubstituted or substituted by at least one alkyl group or a 1-ethoxyethyl group and $R^2$ is as hereinbefore defined) with an alkyl phosphonate of the general formula:

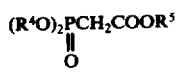

XI (wherein $R^4$ represents a methyl or ethyl group and $R^5$ represents a straight- or branched-chain alkyl group containing from 1 to 10 carbon atoms), optionally hydrolysing the resulting trans-$\Delta^2$-prostaglandin ester of the general formula:

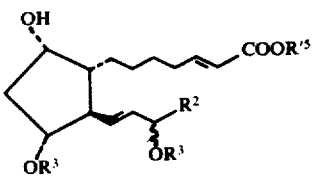

XII (wherein the various symbols are as hereinbefore defined) to the corresponding acid of the general formula:

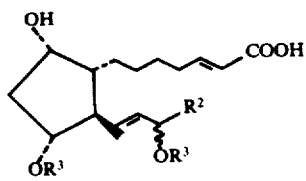

XIII (wherein the various symbols are as hereinbefore defined), converting by methods known per se the 9α- hydroxy group in the compounds of general formula XII and XIII to an oxo group and hydrolyzing the OR³ group in the resulting trans-Δ²-prostaglandin compound of the general formula:

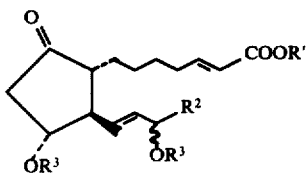

XIV (wherein the various symbols are as hereinbefore defined) to hydroxy groups to obtain a PGE compounds of general formula IX. By the term "methods known per se" as used in this specification is meant methods heretobefore used or described in the chemical literature.

The hydrolysis of the alkyl esters of general formula XII to the corresponding acids of general formula XIII may be carried out according to methods known per se, for example by treatment of the ester with an aqueous solution of an alkali metal, e.g. sodium or potassium, hydroxide or carbonate in the presence of a water-miscible organic solvent, e.g. tetrahydrofuran or an alkanol containing from 1 to 4 carbon atoms, e.g. methanol.

The OR³ groups of the compounds of general formula XIV may be converted to hydroxy groups by mild hydrolysis with an aqueous solution of an organic acid, e.g. acetic acid, or with a dilute aqueous inorganic acid, e.g. hydrochloric acid, advantageously in the presence β- configurations, lead to a separation of the resulting 15α-hydroxy and 15β-hydroxy isomers of formula IX.

The PGF alicyclic ring in the compounds of general formula XII and XIII can be converted into a PGE ring by methods known per se for the conversion of a hydroxy group in the 9-position of a prostaglandin to an oxo group, for example by means of a chromic acid solution (e.g. obtained from chromium trioxide, manganese sulphate and sulphuric acid in water) or Jones' reagent.

The reaction between the cyclopentane derivatives of general formula X and the alkyl phosphonates of general formula XI (in the form of a sodio derivative formed, for example by reaction of sodium hydride with the alkyl phosphonate in an inert organic medium) is carried out under the normal conditions utilized for effecting a Wittig reaction, e.g. in an inert organic solvent at a temperature not exceeding 30° C. The reaction is preferably carried out by suspending a strong base, such as sodium hydride, in an inert organic medium (e.g. tetrahydrofuran or dimethoxymethane), adding the alkyl phosphonate thereby to form its sodio derivative with evolution of a hydrogen gas, and adding to the resulting solution of the sodium alkyl phosphonate the cyclopentane derivative of general formula X. By the Wittig reaction a trans-Δ² double bond is formed stereospecifically and a compound of general formula XII is obtained.

The cyclopentane derivatives of general formula X, which are new compounds and as such constitute a feature of the invention, can be prepared by the series of reactions depicted schematically below:

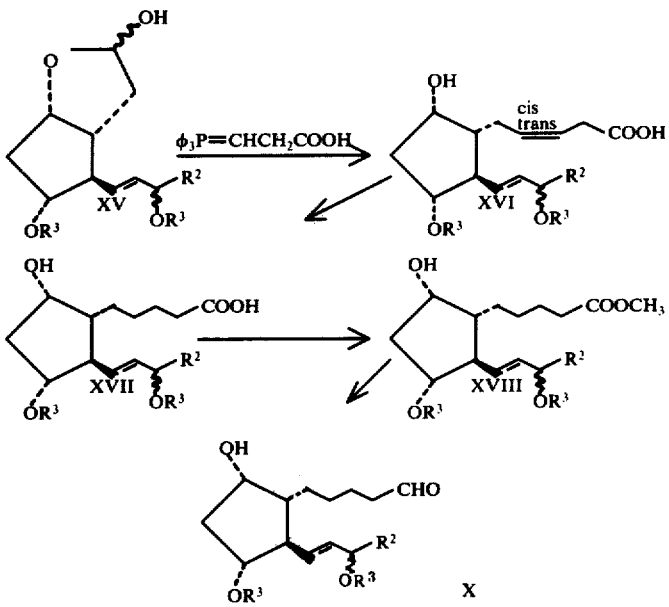

of an organic solvent miscible with water, e.g. tetrahydrofuran or an alkanol containing from 1 to 4 carbon atoms, e.g. methanol. The mild hydrolysis may be carried out at a temperature ranging from ambient to 60° C. preferably at a temperature below 45° C.) with an acid mixture, e.g. a mixture of hydrochloric acid with tetrahydrofuran or methanol, or a mixture of acetic acid, water and tetrahydrofuran. The products of general formula IX may be purified by column chromatography on silica gel, which procedure may, when the starting material of general formula XIV is a mixture of compounds with the OR³ group in the 15-position in α- and wherein φ represents the phenyl group and the other symbols are as hereinbefore defined.

The reaction between the bicyclo-octanes of general formula XV and 2-carboxyethylidenetriphenylphosphorane [obtained by the reaction of sodiomethylsulphinylcarbanide with 2-carboxyethyltriphenylphosphonium bromide, itself prepared from 3-bromopropionic acid and triphenylphosphine] is carried out under the normal conditions utilized for effecting the Wittig reaction, e.g. in an inert solvent at or about ambient temperature. The reaction is preferably carried out in dimethylsulphoxide because the phosphorane compound is practically insoluble in other solvents, e.g. tetrahydrofuran. For the better performance of the Wittig reaction more than two molecular equivalents of the phosphorane compound are required for each mole of the bicyclo-octane reactant. The reaction is generally effected at a temperature of 0° – 40° C., preferably at 20° – 30° C., and is usually complete after about 1 to five hours at laboratory temperature. The acid product of formula XVI (a mixture of cis-$\Delta^3$- and trans-$\Delta^3$-forms) may be extracted from the reaction mixture by conventional procedures and further purified by column chromatography on silica gel.

The catalytic hydrogenation of the compounds of general formula XVI can be carried out as follows The hydrogenation catalyst, i.e., a catalyst usually used for the hydrogenation of double bonds such as various forms of platinum, palladium or nickel, is suspended in an adequate amount of a solvent acting as reaction medium, and the suspension placed in an apparatus appropriate for a catalytic reduction process. The air inside the apparatus is replaced by hydrogen, and a solution of the cyclopentane compound in a suitable inert solvent (for example, methanol, ethanol, water dioxan or acetic acids, or a mixture of two or more of them) is added to the suspension of the catalyst. The reaction takes place at about 0° C. to 50° C. until one or two times the molar quantity of hydrogen has been consumed according to whether or not it is desired to reduce the trans double bond adjacent to the carbon atom carrying the $OR^3$ group in the starting material of formula XVI as well as the cis or trans double bond in $\beta$-position to the carboxy radical, for example for a period of 0.5 to 8 hours. After completion of the reaction, the catalyst is removed by means of a filter, and the filtrate concentrated. If necessary, the residue is purified by column chromatography using silica gel or silica gel impregnated with silver nitrate.

The trans double bond adjacent to the carbon atom carrying the $OR_3$ group is difficult to hydrogenate due to steric hindrance by the tetrahydropyranyloxy or ethoxyethoxy group $OR^3$.

Esterification of the acids of general formula XVII to the methyl esters of general formula XVIII can be effected by methods known per se for converting the carboxy group to a methoxycarbonyl group, for example by reaction with diazomethane in an inert organic solvent, such as diethyl ether, under mild conditions.

The methyl esters of general formula XVIII can be reduced to the corresponding aldehydes of general formula X by methods known per se for converting a methoxycarbonyl group to the formyl group (—CHO), for example by reduction of the methyl esters with diisobutylaluminiumhydride in an inert organic solvent, e.g. toluene, preferably at a low temperature.

The alkyl phosphonate starting materials of general formula XI can be synthesized by the procedure described by G. M. Kosolapoff, J. Amer. Chem. Soc. 68, 1103 (1946), according to the reaction sequence:

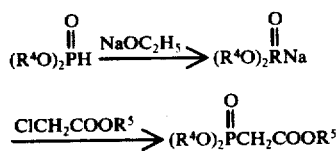

wherein $R^4$ and $R^5$ are as hereinbefore defined.

The compounds of general formula XV can be prepared using initially 2-oxa-3-oxo-6-syn-formyl-7-anti-acetoxy-cis-bicyclo [3,3,0] octane [E. J. Corey et al, J. Amer. Chem. Soc., 91, 5675 (1969)] and the sodio derivative of a dialkyl phosphonate of the general formula:

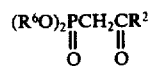   XIX (wherein $R^6$ represents an alkyl group containing from 1 to 4 carbon atoms and $R^2$ is as hereinbefore defined) and applying thereto known procedures [see, for example, J. Amer. Chem. Soc., 92, 397 (1970) and French Pat. No. 7215314 (publication No. 2,134,673)].

The alkyl phosphonates of general formula XIX can be prepared by reacting a solution of n-butyllithium in diethyl ether with a solution of a dialkyl methylphosphonate of the general formula

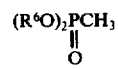   XX (wherein $R^6$ is as hereinbefore defined), e.g. dimethyl methylphosphonate or diethyl methylphosphonate at a temperature below $-50°$ C., and then adding dropwise to the reaction mixture a solution of a compound of the general formula:

   XXI (wherein $R^7$ represents an alkyl group containing from 1 to 4 carbon atoms and $R^2$ is as hereinbefore defined) in tetrahydrofuran at a temperature below $-50°$ C. for 2 $\sim$ 4 hours, and then stirring 2 $\sim$ 18 hours at a temperature ranging from ambient to 0° C. to give the desired dialkyl phosphonate of general formula XIX.

Esters of the trans-$\Delta^2$-prostaglandins of general formula IX can be obtained by reaction of the acids with (i) diazoalkane compounds, e.g. diazomethane, (ii) alcohols in the presence of dicyclohexylcarbodiimide as a condensing agent, or (iii) alcohols following the formation of a mixed acid anhydride by adding a tertiary amine and then a pivaloyl halide or an arylsulphonyl or alkylsulphonyl halide (cf. Belgian Pat. Nos. 775,106 and 776,294).

Compounds of general formula IX wherein $R^1$ represents a hydrogen atom may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e., non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared form acids of general formula IX wherein $R^1$ represents a hydrogen atom by, for example, reaction of stoichiometric quantities of an acid of general formula IX and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

The prostaglandin compounds of general formula IX and corresponding alcohols of general formula IX may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure of by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. $\alpha,\beta$ or $\gamma$-Cyclodextrins or mixtures thereof may be used in the preparation of the cyclodextrin clathrates. Conversion into their cyclodextrin clathrates severes to increase the stability of the prostaglandin compounds.

The prostaglandin analogues of general formula IX and their cyclodextrin clathrates and, when $R^1$ in formula IX represents a hydrogen atom, their non-toxic salts possess the valuable pharmacological properties typical of the prostaglandins is selective fashion in particular, hypotensive activity, abortifacient activity and stimulatory activity on uterine contraction and are useful in the treatment of hypertension, in the treatment of disorders of the peripheral circulation, in the termination of pregnancy and induction of labour in pregnant female mammals and in the control of oestrus, contraception and menstrul regulation in female mammals, and have relatively low potencies in inducing diarrhoea in comparison with their potencies in respect of the valuable properties hereinbefore described and may accordingly be used for those purpose at appropriate rates of administration which do not induce diarrhoea as an undesired side effect.

For example, in standard laboratory tests, on oral administration to the consious spontaneously hypertensive rat, $17(\xi)$-ethyl-$\omega$-bishomo-trans-$\Delta^2$-$PGE_1$ methyl ester produces falls in blood pressure of 15 mmHg, 10 mmHg and 14 mmHg at 0.5, 1 and 3 hours after administration, respectively, at a dose of 0.1 mg/kg. animal body weight, 33 mmHg, 19 mmHg, 13 mmHg and 11 mmHg at 0.5, 1, 3 and 5 hours after administration, respectively, at a dose of 0.3 mg/kg. animal body weight, and 44 mmHg, 39 mmHg, 21 mmHg and 20 mmHg at 0.5, 1, 3 and 5 hours after administration, respectively, at a dose of 1.0 mg/kg. animal body weight.

In the above experiments soft feces were observed only in one out of six rats at the dose of 0.3 mg/kg. animal body weight and in none of six rats and the doses of 0.1 mg/kg. animal body weight and 1.0 mg/kg. animal body weight, respectively. These results indicate that $17(\xi)$-ethyl-$\omega$-bishomo-trans-$\Delta^2$-$PGE_1$ methyl ester has a strong hypotensive activity and a very weak dirrhea-producing (side effect) activity. 16,16-dimethyl-trans-$\Delta^2$-$PGE_1$ methyl ester (i) stimulates uterine contraction when administered intravenously to the pregnant rat on the 20th day of gestation at a dose of 0.5 $\mu$g/kg. animal body weight and (ii) produces fall of the blood-pressure when administered intravenously to the allobarbital-anaesthetized dog at a dose of 1 $\mu$g/kg. animal body weight and (iii) produces diarrhoea at a dose of 1,200 $\mu$g/kg. animal body weight by oral administration in 50% of mice so-treated.

Among various pharmacological activities of 16,16-dimethyl-trans-$\Delta^2$-$PGE_1$ methyl ester, (i) uterine contractile activity is the useful effect and (ii) hypotensive and (iii) diarrhea-producing activities are considered to be undesired effects. Pharmacological activities of 16,16-dimethyl-trans-$\Delta^2$-$PGE_1$ methyl ester and of those compounds already disclosed in the specification of our U.S. application Ser. No. 427,403, e.g. 16(R)-methyl-trans-$\Delta^2$-$PGE_1$, 16($\xi$)-phenyl-$\omega$-trinor-trans-$\Delta^2$ -$PGE_1$ and 15($\xi$)-methyl-trans-$\Delta^2$ -$PGE_1$ are compared in Table 1.

TABLE 1.

|  | (i) Uterine contraction activity $\mu$g/kg | (ii) Hypotensive activity $\mu$g/kg | (iii) Production of diarrhea activity $\mu$g/kg | (ii)/(i) | (iii)/(i) |
|---|---|---|---|---|---|
| 16(R)-methyl-trans-$\Delta^2$-$PGE_1$ | 5 | 0.05 | 85 | 0.05/5 = 0.01 | 85/5 = 17 |
| 16($\xi$)-phenyl-$\omega$-trinor trans-$\Delta^2$-$PGE_1$ | 20 | 0.02 | 1940 | 0.02/20 = 0.001 | 1940/20 = 97 |
| 15($\xi$)-methyl-trans $\Delta^2$-$PGE_1$ | 5 | 1 | 20 | 1/5 = 0.2 | 20/5 = 4 |
| 16,16-dimethyl-trans-$\Delta^2$-$PGE_1$ methyl ester | 0.5 | 1 | 1200 | 1/0.5 = 2 | 1200/0.5 = 2400 |

As noted in Table 1, 16,16-dimethyl-tran-$\Delta^2$-$PGE_1$ methyl ester produces strong desired effect (uterine contraction) which is at least 10 times more potent than other compounds. Moreoever, selectivity index (separation of desired activity from side effects, i.e. (ii)/(i) or (iii)/(i) ratio) of 16,16-dimethyl-trans-$\Delta^2$-$PGE_1$ methyl ester is very much higher than those of other compounds. These data indicate that 16,16-dimethyl-trans-$\Delta$2-$PGE_1$ methyl ester is a strong and safe compound which can not be expected from those compounds already disclosed in the specification of our U.S. patent application Ser. No. 427,403.

The following Reference Examples and Examples illustrate the preparation of new prostaglandin analogues of the present invention.

REFERENCE EXAMPLE 1

Synthesis of 2-carboxyethyl-triphenylphosphonium bromide

A solution of 90 g. of triphenylphosphine and 50 g. of 3-bromopropionic acid in 550 ml. of acetonitrile was refluxed for two days. The reaction mixture was then distilled under reduced pressure to remove acetonitrile, and the residue was stirred well together with diethyl ether, and then the upper ethereal layer remoVed by decantation. The operation was repeated twice to form the crystalline product, which was recrystallised from acetonitriles, yield of the title compound: 115 g, m.p. 195°–198° C. Infra-red (hereinafter abbreviated to IR) absorption spectrum (potassium bromide tablet) 2880, 1740, 1434, 1382, 1322, 1230, 1105, 745, 690, 520 and 505 cm$^{-1}$.

REFERENCE EXAMPLE 2

Synthesis of 9α-hydroxy-11α,15α-bis-(2-tetrahydropyranyloxy)-16,16-dimethyl-α-dinor-prost-trans-13-enoic acid A solution of 92 g. of 2-carboxyethyltriphenylphosphonium bromide (prepared as described in Reference Example 1) in 200 ml. of dimethylsulphoxide was mixed with 200 ml. of dimethylsulphoxide containing 2.1 moles of sodiomethylsulphinyl carbanide (0.42 mole as sodiomethylsulphinyl cabanide) whilst maintaining the temperature at 25° C. To the resulting red mixture was added 150 ml. of a solution containing 34 g. of 2-oxa-3-hydroxy-6-syn-(3α-2'-tetrahydropyranyloxy-4,4-dimethyl-oct-trans-1-enyl)-7-anti-(2-tetrahydropyranyloxy)-cis-bicyclo[3,3,0]octane [prepared as described in Great Britain Pat. No. 1,398,291, Reference Example 8] in dimethylsulphoxide. The resulting mixture was stirred for 2 hours at 25° C. and 1 hour at 40° C, and then poured into a mixture of 3.5 liters of ice-water, 500 ml. of diethyl ether and 6 g. of potassium carbonate, and extracted with ethyl acetate. The aqueous layer was extracted three times with a mixture of diethyl ether and ethyl acetate (1:1) to remove the neutral substances. The aqueous layer was adjusted to pH 2 with oxalic acid and extracted 4 times with diethyl ether-pentane mixture (1:1), and the extract was washed with water, dried and concentrated under reduced pressure. The residue was purified by silica gel column chromatography using ethanol-benzene mixture (1:20) as eluent to give 9α-hydroxy-11α,15α-bis-(2-tetrahydropyranyloxy)-16,16-dimethyl-α-dinor-prosta-cis-and trans-5,trans-13-dienoic acids as a colorless oil in a yield of 12 g. Thin layer chromatography (hereinafter abbreviated to TLC); (developing solvent, methylene-chloride:methanol = 19:1) Rf = 0.21.

The product was dissolved in 300 ml. of methanol, mixed with 4 g. of 5% palladium carbon and treated with an equimolar amount of hydrogen at room temperature. The reaction mixture was filtered with a glass filter to remove the catalyst and the filtrate concentrated under reduced pressure to yield the title compound 12 g.

REFERENCE EXAMPLE 3

Synthesis of 9α-hydroxy-11α,15α-bis-(2-tetrahydropyranyloxy)-17(ξ)-ethyl-α-dinor-ω-dihomo-prost-trans-13-enoic acid Using 2-oxa-3-hydroxy-6-syn-(3α-2'-tetrahydropyranyloxy-5(ξ)-ethyl-dec-trans-1-enyl)-7-anti-(2-tetrahydropyranyloxy)-cis-bicyclo[3,3,0]octane, the title compound was obtained by the same procedure as described in Reference example 2.

The starting material was synthesized as follows.

65 g. of dimethyl methyl phosphonate was dissolved in 465 ml. of tetrahydrofuran and cooled to −70° C. in nitrogen atmosphere. The solution of butyl lithium produced from 85.3 g. of butyl bromide and 10.7 g. of lithium in 400 ml. of diethyl ether was added dropwise into the above solution during about 15 minutes at the temperature below −50° C. After stirring for 10 minutes, 44 g. of ethyl 3(ξ)-ethyl-octanoate in 140 ml. of tetrahydrofuran was added dropwise at the temperature below −50° C., the mixture was stirred at the same temperature for 2 hours and then at the room temperature for further 2 hours and then 92 g. of acetic acid was added. Then the reaction mixture was concentrated under reduced pressure and the residue was dissolved in water, extracted with ether, and the ether extract was washed with water, dried over magnesium sulfate and concentrated under reduced pressure. The residue was distilled under reduced pressure. b.p. 113°–121° C/0.2 mmHg. 55 g. of the dimethyl-2-oxo-4-ethyl-nonylphosphonate was obtained as a colorless oil. IR absorption spectrum (liquid film): 2950, 2860, 1710, 1455, 1270, 1190, 1040 and 820 cm$^{-1}$.

9.42 g. of sodium hydride (content 50%) was suspended in 1.55 liters of tetrahydrofuran and 55 g. of the compound hereinabove obtained in 210 ml. of tetrahydrofuran was added into the suspension, and stirred at room temperature. When the evaluation of hydrogen gas was ceased and the suspension became transparent, 41.5 g. of 2-oxa-3-oxo-6-syn-formyl-7-anti-acetoxy-cis-bicyclo[3,3,0]octane in 520 ml. of tetrahydrofuran was added and stirred at room temperature for 2 hours and acidifid with glacial acetic acid to pH 4 and the formed precipitate was filtered off, the filtrate was concentrated under reduced pressure and the residue was purified by silica gel column chromatography using benzene-ethyl acetate (5:1). 62 g. of the 2-oxa-3-oxo-6-syn-(3-oxo-5(ξ)-ethyl-dec-trans-1-enyl)-7-anti-acetoxy-cisbicyclo[3,3,0]octane was obtained.

TLC (developing solvent, benzene:diethyl ether:methanol = 5:1:1) Rf = 0.71; IR absorpton spectrum (liquid film) 2950, 2930, 2860, 1775, 1740, 1690, 1665, 1620, 1240, 1170 and 980 cm$^{-1}$;

Nuclear magnetic resonance (hereinafter abbreviated to NMR) spectrum (CCl$_4$ solution): 6.50–5.80 (2H, m), 5.10–4.70 (2H, m), 2.02 (3H, s), 1.10–0.60 (6H, m).

The compound hereinabove obtained 62 g. was dissolved in 600 ml. of dimethoxy ethane, and reduced with 180 ml. of a solution of 0.55 M-zinc borohydride in dimethoxy ethane at 20° C. for 30 minutes and the crude product was purified by silica gel column chromatography using diethyl ether-hexane-ethyl acetate (2:1:1). 12.5 g. of 2-oxa-3-oxo-6-syn(3α-hydroxy-5(ξ)-ethyl-dec-trans-1-enyl)-7-anti-acetoxy-cisbicyclo [3,3,0]octane was obtained.

TLC (developing solvent, methylene chloride:methanol = 19:1) Rf = 0.42;

IR absorption spectrum (liquid film) 3460, 2950, 2870, 1770, 1740, 1370, 1240, 1180 and 975 cm$^{-1}$ NMR spectrum (CCl$_4$ solution): 5.50–5.30 (2H, m), 5.10–4.60 (2H, m), 4.10–3.80 (1H, m), 2.03 (3H, s), 1.10–0.45 (6H, m).

12.5 g. of the compound hereinabove obtained was hydrolyzed with equal mols of potassium carbonate in methanol at 25° C. for 15 minutes to obtain 10.8 g. of 2-oxa-3-oxo-6-syn-(3α-hydroxy-5(ξ)-ethyl-dec-trans-1-enyl)-7-anti-hydroxy-cisbicyclo[3,3,0]octane as a pale-yellow oil.

TLC (developing solvent, methylenechloride:methanol = 19:1) RF = 0.30;

IR absorption spectrum (liquid film): 3400, 2950, 2860, 1775, 1180, 1090, 1040 and 975 cm$^{-1}$;

NMR spectrum (CDCl$_3$ solution): 5.50–5.30 (2H, m), 5.00–4.60 (1H, m), 4.10–3.60 (4H, m), 1.05–0.40 (6H, m).

10.8 g. of the compound hereinabove described was dissolved in 95 ml. of methylene chloride and was reacted with three times the molar quantity of dihydropyrane in the presence of a trace amount of p-toluenesulfonic acid at 25° C. for 15 minutes to obtain 17 g. of 2-oxa-3-oxo-6-syn-(3α-2'tetrahydropyranyloxy-5(ξ)-ethyl-dec-trans-1-enyl)-7-anti-(2-tetrahydropyranyloxy)-cisbicyclo[3,3,0]octane was obtained.

TLC (developing solvent, methylenechloride:methanol = 19:1) RF = 0.74;

IR absorption spectrum (liquid film): 2930, 2860, 1775, 1120, 1080, 1040, 1025 and 980 cm$^{-1}$;

NMR spectrum (CDCl$_3$ solution): 5.50–5.20 (2H, m), 5.10–4.70 (1H, m), 4.70–4.40 (2H, m), 1.05–0.45 (6H, m).

17 g. of the compound hereinabove described was reduced with twice the molar quantity of diisobutylaluminum hydride in toluene at −60° C. for 30 minutes to obtain 16 g. of 2-oxa-3-hydroxy-6-syn-(3α-2'-tetrahydropyranyloxy-5(ξ)-ethyl-dec-trans-1-enyl)-7-anti-(2-tetrahydropyranyloxy)-cisbicyclo[3,3,0]-octane as the starting material was obtained.

TLC (developing solvent, methylenechloride:methanol = 19:1) RF = 0.39;

IR absorption spectrum (liquid film) 3420, 2950, 2860, 1120, 1080, 1040, 1020 and 980 cm$^{-1}$;

NMR spectrum (CDCl$_3$ solution) 5.70–5.20 (2H, m), 4.70–4.30 (3H, m), 1.10–0.45 (6H, m).

REFERENCE EXAMPLE 4

Synthesis of methyl 9α-hydroxy-11α,15α-bis-(2-tetrahydropyranyloxy)-16,16-dimethyl-α-dinor-prost-trans-13-enoate To a solution of 6 g. of 9α-hydroxy-11α,15α-bis-(2-tetrahydropyranyloxy)-16,16-dimethyl-α-dinor-prost-trans-13-enoic acid in 100 ml. of diethyl ether was added a newly prepared solution of diazomethane in diethyl ether until the reaction mixture became yellow. The reaction mixture was then concentrated under reduced pressure and low temperature, and the residue purified by means of silica gel column chromatography using an ethyl acetate-cyclohexane mixture (1:1) as eluent to yield 4.92 g. of the title compound as a colourless oil.

TLC (developing solvent, ethyl acetate-cyclohexane = 1:1) RF = 0.59;

REFERENCE EXAMPLE 5

Synthesis of methyl 9α-hydroxy-11α,15α-bis-(2-tetrahydropyranyloxy)-17(ξ)-ethyl-α-dinor-ω-bishomo-prost-trans-13-enoate By the same procedure as described in Reference example 4, 4.7 g. of the title compound was obtained from 5.6 g. of 9α-hydroxy-11α,15α-bis-(2-tetrahydropyranyloxy)-17(ξ)-ethyl-α-dinor-ω-bishomo-prost-trans-13-enoic acid (prepared as described in Reference Example 3) as a colourless oil.

TLC (developing solvent, ethyl acetate:cyclohexane = 1:1) RF = 0.59;

IR absorption spectrum (liquid film): 3400, 2940, 2860, 1740, 1080, 1020 and 980 cm$^{-1}$;

NMR spectrum (CDCl$_3$ solution) 5.70–5.50 (2H, m), 4.70–4.50 (2H, m), 3.65 (3H, s), 1.10–0.45 (6H, m).

REFERENCE EXAMPLE 6

Synthesis of 9α-hydroxy-11α,15α-bis-(2-tetrahydropyranyloxy)-16,16-dimethyl-α-dinor-prost-trans-13-enaldehyde A solution of 8 g. of the product of Reference example 4 in 230 ml. of toluene was cooled to −65° C., mixed with 34 ml. of a toluene solution containing diisobutylaluminium hydride (25 w/v %), and the reaction mixture stirred for 30 minutes at the same temperature. Methanol was gradually added dropwise and, after the bubbling stopped, the resulting mixture was raised to 0° C. then stirred with 50 ml. of water for 30 minutes. The aluminium hydroxide which formed was filtered off and the filtrate was washed with aqueous sodium chloride solution, dried over magnesium sulphate and concentrated at reduced pressure to obtain the title compound as a colourless oil. Yield was 8 g.

TLC (developing solvent, ethyl acetate:cyclohexane = 1:1) RF = 0.44;

REFERENCE EXAMPLE 7

Synthesis of 9α-hydroxy-11α,15α-bis-(2-tetrahydropyranyloxy)-17(ξ)-ethyl-α-dinor-ω-bishomo-prost-trans-13-enaldehyde By the same procedure as described in Reference example 6, 4.4 g. of the title compound was obtained from 4.7 g. of the product of Reference example 5 as a colourless oil.

TLC (developing solvent, ethyl acetate:cyclohexane = 1:1) RF = 0.51.

EXAMPLE 1

Synthesis of 9α-hydroxy-11α,15α-bis-(2-tetrahydropyranyloxy)-16,16-dimethyl-prosta-trans-2,trans-13-dienoic acid ethyl ester To a mixture of 1.02 g. (content 65%) of sodium hydride and 110 ml. of tetrahydrofuran was added dropwise 6.2 g. of triethylphosphonoacetate, the reaction mixture being maintained at a temperature less than 30° C. Stirring was continued at 25° C. for 30 minutes until the generation of hydrogen stopped. 4 g. of the product of Reference example 6 in 135 ml. of tetrahydrofuran was added thereto, and the resulting mixture was stirred for 50 minutes at 25° C., adjusted to pH 7 with acetic acid, diluted with water, extracted with diethyl ether and the ethereal extract washed with water, dried and concentrated. The residue was purified by silica gel of column chromatography using an ethyl acetate-cyclohexane mixture (1:3) as eluent to obtain 4 g. of the title compound as a colourless oil.

TLC (developing solvent, ethyl acetate:cyclohexane = 1:1) RF = 0.55.

EXAMPLE 2

Synthesis of ethyl 9α-hydroxy-11α,15α-bis-(2-tetrahydropyranyloxy)-17(ξ)-ethyl-prosta-trans-2,trans-13-dienoate By the same procedure as described in Example 1, 4.8 g. of the title compound was obtained from 4.7 g. of the product of Reference example 7 as a colourless oil.

TLC (developing solvent, ethyl acetate:cyclohexane = 1:1) RF = 0.66;

IR absorption spectrum (liquid film): 3450, 2850, 1725, 1650, 1430, 1320, 1235, 1125, 1070, 1015 and 975 $cm^{-1}$.

EXAMPLE 3

Synthesis of 9-Oxo-11α,15α-bis-(2-tetrahydropyranyloxy)-16,16-dimethyl-prosta-trans-2,trans-13-dienoic acid 4 g. of ethyl 9α-hydroxy-11α,15α-bis-(2-tetrahydropyranyloxy)-16,16-dimethyl-prosta-trans-2trans-13-dienoate (prepared as described in Example 1) were dissolved in 130 ml. of a mixture of ethanol-water (3:1), mixed with 3.9 g. of potassium hydroxide and stirred at 25° C. for 2 hours. The reaction mixture was acidified with aqueous solution of oxalic acid to pH 5, and diluted with 100 ml. of water, extracted with ethyl acetate. The extracts were washed with water, dried over sodium sulphate and concentrated under reduced pressure to obtain 3.88 g. of 9α-hydroxy-11α,15α-bis-(2-tetrahydropyranyloxy)-16,16-dimethyl-prosta-trans-2,trans-13-dienoic acid.

TLC (developing solvent, ethyl acetate-cyclohexane = 1:1) Rf = 0.18.

The obtained compound 2.46 g. were dissolved in 72 ml. of diethyl ether and stirred at 3° C. To which, a solution of manganese sulphate (15 g.), 3.1 g. of chromium trioxide, 72 ml. of water and 3.5 ml. of suphuric acid was added. After stirring for 3.5 hours at 3° C., extracted with diethyl ether. The organic layer was washed with water, dried over sodium sulphate and concentrated under reduced pressure. The residue was purified by column chromatography on silica gel using ethyl acetate-benzene (1:1) as eluent to give 2.35 g. of the title compound having the following physical characteristics.

TLC (developing solvent, methylene chloride:methanol = 20:1) Rf = 0.24;

IR (liquid film): 2925, 2850, 1740, 1690, 1645, 1445, 1375, 1350, 1240, 1140, 1090, 1045 and 980 $cm^{-1}$.

EXAMPLE 4

Synthesis of 9-Oxo-11α,15α-bis-(2-tetrahydropyranyloxy)-17(ξ)-ethyl-ω-bishomo-propsta-trans-2,-trans-13-dienoic acid By the same procedure as described in Example 3, 676 mg. of the title compound were obtained from 1.31 g. of methyl 9α-hydroxy-11α,15α-bis-(2-tetrahydropyranyloxy)-17(ξ)-ethyl-ω-bishomo-prosta-trans-2,trans-13-dienoate.

TLC (developing solvent, methylene chloride:methanol = 20:1): Rf = 0.22;

IR (liquid film): 2930, 2840, 1740, 1690, 1645, 1450, 1375, 1350, 1240, 1140, 1085, 1045, 1035 and 980 $cm^{-1}$;

NMR ($CDCl_3$ solution): 9.40 (1H, broad s), 7.05 (1H, dt), 5.80 (1H, d), 5.85–5.30 (2H, m), 5.00–4.50 (2H, m), 4.50–3.20 (6H, m).

EXAMPLE 5

Synthesis of 16,16-dimethyl-trans-$\Delta^2$-$PGE_1$ 2.35 g. of the bis-tetrahydropyranyl ether prepared as described in Example 3 were dissolved in 6 ml. of tetrahydrofuran and 60 ml. of 65%-acetic acid aqueous solution and the solution stirred at 60 to 70° C. for 20 minutes. The reaction mixture was extracted with ethyl acetate, and the organic layer was washed with water, dried and concentrated under reduced pressure. The residue was purified by column chromatography on silica gel using ethyl acetate-cyclohexane (2:3) as eluent to yield 270 mg. of the title compound.

TLC (developing solvent, tetrahydrofuran:chloroform:acetic acid = 2:10:1): Rf = 0.30.

EXAMPLE 6

Synthesis of 17(ξ)-ethyl-trans-$\Delta^2$-ω-bishomo-$PGE_1$

By the same procedure as described in Example 5, 313 mg. of the title compound were obtained from 676 mg. of the bis-tetrahydropyranyl ether prepared as described in Example 4.

TLC (developing solvent, tetrahydrofuran:chloroform:acetic acid = 2:10:1): Rf = 0.28.;

IR (liquid film): 3350, 2930, 2850, 1745, 1700, 1655, 1460, 1420, 1385, 1170, 1090 and 985 $cm^{-1}$;

NMR ($CDCl_3$ solution): 6.99 (1H, dt), 5.78 (1H, d), 5.90 (3H, broad s), 5.70–5.40 (2H, m), 4.40–3.78 (2H, m), 2.95–2.55 (1H, dd).

EXAMPLE 7

Synthesis of 16,16-dimethyl trans-$\Delta^2$-$PGE_1$ methyl ester 50.8 mg of 16,16-dimethyl-trans-$\Delta^2$-$PGE_1$ (prepared as described in Example 5) were dissolved in 3 ml. of diethyl ether, and to the solution of a freshly prepared ethereal solution of diazomethane was added so that the reaction mixture turned yellow. The reaction mixture was concentrated under reduced pressure at low temperature, and the residue purified by column chromatography on silica gel using ethyl acetate-cyclohexane (1:3) as eluent to give 40 mg. of the title compound.

TLC (developing solvent, chloroform:tetrahydrofuran:acetic acid = 10:2:1) Rf = 0.36

IR (liquid film) 3400, 2940, 2850, 1750, 1730, 1660, 1440, 1280 $cm^{-1}$.

EXAMPLE 8

Synthesis of 17(ξ)-ethyl-trans-$\Delta^2$-ω-bishomo-$PGE_1$ methyl ester

By the same procedure as described in Example 7, 97 mg. of the title compound were obtained from 130 mg. of the 17(ξ)-ethyl-trans-$\Delta^2$-ω-bishomo-$PGE_1$ (prepared as described in Example 6).

TLC (developing solvent, chloroform:tetrahydrofuran:acetic acid = 10:2:1) Rf = 0.33;

IR (liquid film): 3470, 2920, 2840, 1735, 1720, 1650, 1450, 1430, 1270, 1165, 1080 and 980 $cm^{-1}$;

NMR ($CDCl_3$ solution): 6.93 (1H, dt), 5.79 (1H, d), 5.67–5.40 (2H, m), 4.37–3.83 (2H, m), 3.71(3H, s), 2.92–2.53 (1H, dd), 1.06–0.65 (6H, m).

The present invention includes within its scope pharmaceutical compositions which comprise at least one new therapeutically useful prostaglandin compound according to the present invention, together with a pharmacuetical carrier or coating. In clinical practice the new compounds of the present invention will normally be administered orally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid composition for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include a adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In human adult, the doses per person are generally between 0.01 and 1 mg. by oral administration in the treatment of hypertension, between 1 - 1000 µg. of oral, intravaginal, intravenous and extraamniotic administration for the contraception and menstrual regulation in females and in the termination of pregnancy and the induction of labour in pregnant females.

In domestic female mammals such as cows, mares, sows, ewes and bitches, the doses are generally between 0.001 and 50 mg./animal by intramuscular, subcutaneous, intrauterine, intravaginal and intravenous administration for the synchronisation of oestrus, treatment of impaired fertility and the induction of abortion and of labour.

The following Example illustrates the pharmaceutical composition according to the invention.

EXAMPLE 9

16,16-dimethyl-trans-$\Delta^2$-PGE$_1$ methyl ester (2 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 µg. of 16,16-dimethyl-trans-$\Delta^2$-PGE$_1$ methyl ester which after swallowing of the capsule is released into he stomach.

We claim:

1. 16,16-dimethyl-trans-$\Delta^2$-PGE$_1$ or the $C_1$–$C_{10}$ alkyl esters, cyclodextrin clathrate, or non-toxic salt thereof.

2. The methyl ester of the compound defined in claim 1.

3. A composition useful for regulating the menstrual cycle which comprises, as active ingredient, at least one trans-$\Delta^2$-prostaglandin as claimed in claim 1 or a cyclodextrin clathrate thereof or a non-toxic salt of a trans-$\Delta^2$-prostaglandin as claimed in claim 1, in association with pharmaceutical carrier.

* * * * *